US009072555B2

(12) United States Patent
Michel

(10) Patent No.: US 9,072,555 B2
(45) Date of Patent: Jul. 7, 2015

(54) CARBON FIBER REINFORCED PEEK BONE PLATE WITH TITANIUM FIXATION SCREWS

(75) Inventor: Gerlinde Michel, Munich (DE)

(73) Assignee: Arthrex, Inc., Naples, FL (US)

( * ) Notice: Subject to any disclaimer, the term of this patent is extended or adjusted under 35 U.S.C. 154(b) by 808 days.

(21) Appl. No.: 12/504,130

(22) Filed: Jul. 16, 2009

(65) Prior Publication Data

US 2010/0016858 A1    Jan. 21, 2010

Related U.S. Application Data

(60) Provisional application No. 61/082,408, filed on Jul. 21, 2008.

(51) Int. Cl.
| | |
|---|---|
| *A61B 17/80* | (2006.01) |
| *A61B 17/17* | (2006.01) |
| *A61B 17/86* | (2006.01) |
| *A61B 17/02* | (2006.01) |

(52) U.S. Cl.
CPC ......... *A61B 17/8057* (2013.01); *A61B 17/1728* (2013.01); *A61B 17/8605* (2013.01); *A61B 17/8635* (2013.01); *A61B 2017/0256* (2013.01); *A61B 17/8095* (2013.01); *A61B 17/1764* (2013.01)

(58) Field of Classification Search
CPC ........... A61B 17/8057; A61B 17/8095; A61B 17/1728; A61B 17/8605; A61B 17/1764; A61B 17/8635; A61B 2017/0256
See application file for complete search history.

(56) References Cited

U.S. PATENT DOCUMENTS

| | | | | |
|---|---|---|---|---|
| 5,613,969 | A * | 3/1997 | Jenkins, Jr. | 606/87 |
| 5,620,448 | A | 4/1997 | Puddu | |
| 5,749,875 | A * | 5/1998 | Puddu | 606/87 |
| 5,769,850 | A * | 6/1998 | Chin | 606/53 |
| 5,879,161 | A * | 3/1999 | Lazzara | 433/173 |
| 6,342,055 | B1* | 1/2002 | Eisermann et al. | 623/17.16 |
| 6,565,570 | B2* | 5/2003 | Sterett et al. | 606/280 |
| 6,823,871 | B2* | 11/2004 | Schmieding | 128/898 |
| 6,955,677 | B2 | 10/2005 | Dahners | |
| 7,326,218 | B2* | 2/2008 | Sterett et al. | 606/105 |

(Continued)

FOREIGN PATENT DOCUMENTS

WO    WO 2007/014279 A2    2/2007

OTHER PUBLICATIONS

Signus Medical ECF PEEK—Optima plate with "Endless Carbon Fiber", Signus Medical LLC, www.signusmedical.com (2008).

*Primary Examiner* — Matthew Lawson
*Assistant Examiner* — Zade Coley
(74) *Attorney, Agent, or Firm* — Dickstein Shapiro LLP

(57) ABSTRACT

Apparatus and methods for tissue fixation using a bone plate configured to accommodate fixation devices (such as screws, for example) inserted at various angles. The bone plate is formed of a material softer than the material of the fixation devices, and is provided with fixation holes with rounded, curved interior walls (i.e., non-threaded holes) that allow the fixation devices to be inserted at various angles. The fixation holes have a diameter smaller than that of the fixation devices. As a result of the difference between the materials of the plate and of fixation devices, and of the difference between the diameters of the fixation holes and of the fixation devices, the fixation devices deform the interior walls of the fixation holes, therefore self-threading the holes at an advantageous angle.

15 Claims, 13 Drawing Sheets

(56) References Cited

U.S. PATENT DOCUMENTS

| | | | |
|---|---|---|---|
| 2002/0133157 A1* | 9/2002 | Sterett et al. | 606/69 |
| 2004/0073218 A1 | 4/2004 | Dahners | |
| 2005/0015089 A1* | 1/2005 | Young et al. | 606/69 |
| 2005/0209599 A1* | 9/2005 | Brunsvold | 606/87 |
| 2005/0234458 A1* | 10/2005 | Huebner | 606/69 |
| 2006/0116678 A1* | 6/2006 | Impellizzeri | 606/69 |
| 2006/0149264 A1 | 7/2006 | Castaneda et al. | |
| 2006/0200147 A1 | 9/2006 | Ensign | |
| 2006/0235400 A1 | 10/2006 | Schneider | |
| 2008/0051791 A1* | 2/2008 | Young et al. | 606/69 |

* cited by examiner

CARBON FIBER REINFORCED PEEK BONE PLATE WITH TITANIUM FIXATION SCREWS

CROSS-REFERENCE TO RELATED APPLICATIONS

This application claims the benefit of U.S. Provisional Application No. 61/082,408, filed Jul. 21, 2008, the entire disclosure of which is incorporated by reference herein.

FIELD OF THE INVENTION

The present invention relates to a carbon fiber reinforced PEEK bone plate with titanium fixation screws, and to a method for performing high tibial open wedge osteotomy using the bone plate.

BACKGROUND OF THE INVENTION

Treatment of pain or instability associated with lower extremity misalignment may require surgical interventions, such as osteotomy. High tibial osteotomies are indicated by early, medial joint-space narrowing, by early arthritis in patients who have had previous medial meniscectomy, or following rupture of the anterior cruciate ligament in patients with pre-existing varus deformity, for example.

Two osteotomy methods are known in the art: the closed wedge method, and the open wedge method. In the closed wedge method, removal of a bone wedge creates an angled gap in the bone. Part of the bone is left as a hinge at the apex of the angle. The hinge allows the gap to narrow, and the bone material on either side of the closed gap joins together. In the open wedge method, a cut is made across the bone. Part of the bone is left as a hinge, as in the closed wedge method. In contrast to the closed wedge method, however, the hinge allows the cut gap to open. The open wedge is filled with graft material. The two osteotomy methods are performed on opposite sides of the bone to give equivalent results. For example, when a given deformity would be corrected by performing the open wedge procedure on the medial side of a bone, an equivalent closed wedge correction would be performed laterally.

The closed wedge method is the current standard, although several disadvantages are associated with this technique. The most significant disadvantages of the closed wedge method are: (1) disruption of the tibial-femoral joint; (2) possible damage to neurovascular structures; and (3) disruption of the medial cortex, resulting in instability and nonunion between the upper and lower bone because of possible soft tissue interference. It is also difficult to compute the correct amount of bone to remove and, therefore, several extra cuts may be required.

The open wedge method avoids or mitigates many of the disadvantages associated with the closed wedge method. Additionally, the medial, open-wedge high tibial osteotomy has the following advantages over the closed, lateral-wedge high tibial osteotomy: (1) speed; (2) simplicity; (3) ability to quickly change angle at any time during the procedure; and (4) no requirement for fibular osteotomy. Open wedge osteotomy procedures are disclosed, for example, in U.S. Pat. No. 5,620,448 and U.S. Pat. No. 5,749,875, both of which are assigned to Arthrex, Inc. and incorporated herein by reference.

Because the open wedge method leaves a gap in the bone, a brace is necessary to fix the portions on either side of the gap relative to each other and bear weight until new bone grows to fill the gap. Conventionally, the brace is a bone plate formed of stainless steel or titanium. The bone plate is typically affixed to the bone portions on either side of the gap with steel or titanium screws inserted through pre-formed screw holes in the bone plate. One such bone plate is disclosed in U.S. Pat. No. 5,749,875 referenced above.

Because conventional bone plates are formed of a hard metallic material (e.g., stainless steel or titanium), they offer sufficient strength but the angle at which screws must be inserted is fixed, either by threading or by providing a tapered portion on the interior of the screw holes. This is disadvantageous because it may prevent a surgeon from adjusting the insertion angle of the fixation screws to better accommodate the curvature of a patient's bone. Thus, there is a need in the art for a bone plate that can accommodate fixation screws inserted at different angles.

SUMMARY OF THE INVENTION

The present invention provides apparatus and methods for tissue fixation using a bone plate configured to accommodate fixation devices (such as screws, for example) inserted at various angles.

The bone plate is formed of a material softer than the material of the fixation devices, and is provided with fixation apertures or holes with rounded, curved interior walls (i.e., non-threaded holes) that allow the fixation devices to be inserted at various angles. The fixation apertures or holes have a diameter smaller than that of the fixation devices. As a result of the differences between the materials of the plate and of fixation devices, and between the diameters of the fixation holes and of the fixation devices, the fixation devices deform the interior walls of the fixation holes, therefore "self-threading" the holes at an advantageous angle. The "self-threading" of the fixation holes of the plate by the fixation devices eliminates the need for prior threading or tapering of the fixation holes.

Other features and advantages of the present invention will become apparent from the following description of the invention, which refers to the accompanying drawings.

DETAILED DESCRIPTION OF THE PREFERRED EMBODIMENTS

Figure 1:
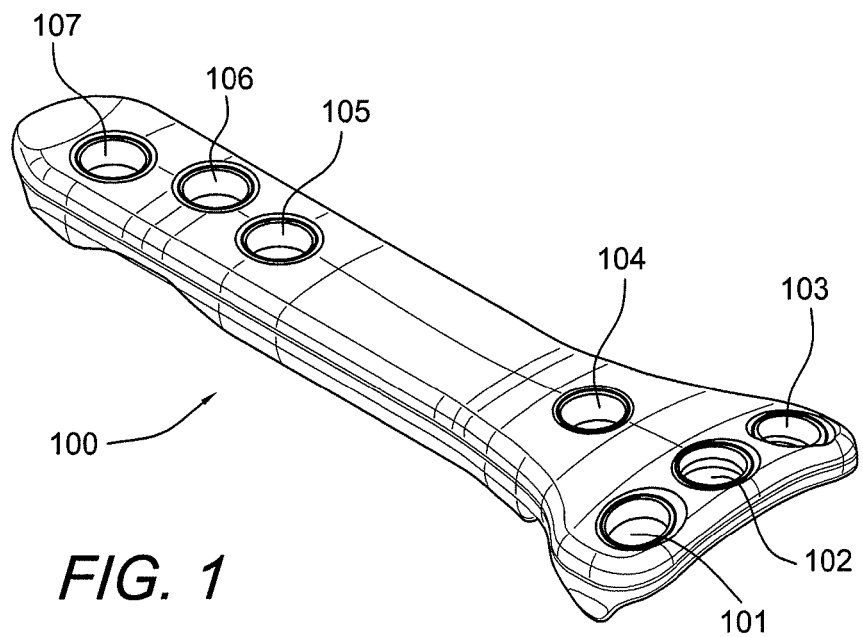
FIG. 1 is a perspective view of a bone plate according to a first embodiment of the present invention.

In the following detailed description, reference is made to various specific embodiments in which the invention may be practiced. These embodiments are described with sufficient detail to enable those skilled in the art to practice the invention, and it is to be understood that other embodiments may be employed, and that structural and logical changes may be made without departing from the spirit or scope of the present invention.

The present invention provides apparatus and methods for tissue fixation (for example, tissue to bone fixation) using a bone plate configured to accommodate fixation devices (such as screws, for example) inserted at various angles. The bone plate is formed of a material softer than the material of the fixation devices, and is provided with fixation apertures or holes with rounded, curved interior walls (i.e., non-threaded holes) that allow the fixation devices to be inserted at various angles. As a result of the difference between the material of the plate and that of the fixation devices, the "self-threading" of the fixation holes of the plate by the fixation devices (i.e., by the threaded screws) eliminates the need for prior threading or tapering of the fixation holes.

According to exemplary embodiments of the present invention, the bone plates of the present invention are configured to accommodate fixation screws inserted at various angles, by forming the bone plate of a softer material than the screws, and rounding the interior walls of the screw holes in the bone plate. Because the bone plate is softer than the fixation screws, the harder fixation screws will deform the interior walls of the screw holes during insertion. This "self-threading" of the screw apertures or holes by the fixation screws eliminates the need for prior threading or tapering of the screw apertures or holes. The curvature (i.e., rounding) of the interior walls of the screw holes (which is described in greater detail below with reference to FIG. 5, for example) allows fixation screws to be inserted at a range of angles. Thus, the surgeon is free to select a preferable screw insertion angle during the osteotomy based, for example, on the shape of the patient's bone.

The bone plate and fixation screws must be sufficiently strong to endure post-operative forces exerted upon them by a patent's weight and movement. In an exemplary embodiment only, the bone plate is formed of polyetheretherketone ("PEEK") reinforced with a biocompatible fiber filler. In a preferred embodiment, the bone plate is formed of carbon fiber reinforced PEEK (also known as "CF-PEEK").

The formation of the bone plate of ordinary PEEK (i.e., without carbon fiber reinforcement) would cause the bone plate to be too soft and unable to bear sufficient weight. Similarly, fixation devices (for example, fixation screws) formed of PEEK, or even CF-PEEK, would not be sufficiently strong. Therefore, metallic fixation devices (such as metallic screws) are preferred. In an exemplary embodiment, the fixation devices include at least one screw that comprises titanium, most preferably in the form of $TiAl_6V_4$ (i.e., a titanium alloy comprising about 6% aluminum and about 4% vanadium) which provides high strength, light weight, and corrosion resistance. In an exemplary embodiment, all fixation devices are screws.

Referring now to the drawings, where like elements are designated by like reference numerals, FIGS. 1-22 illustrate embodiments of bone plates 100, 200 of the present invention that comprise carbon fiber reinforced PEEK and are provided with fixation apertures or holes with rounded, curved interior walls (i.e., non-threaded holes) that allow corresponding fixation devices (such as fixation screws, for example) to be inserted at various angles. The fixation devices used in conjunction with the bone plates 100, 200 of the present invention are preferably formed of a material stronger than the material of the bone plates (i.e., stronger than carbon fiber reinforced PEEK). Exemplary materials for the fixation devices are, for example, titanium, titanium alloys, stainless steel, or combinations of such materials.

FIG. 1 illustrates the top and side of a bone plate 100 (i.e., the side facing away from the bone after installation) constructed in accordance with a first embodiment of the present invention. The bone plate 100 is preferably constructed of carbon fiber reinforced PEEK. Proximal apertures or holes 101, 102, 103 (proximal fixation holes or proximal screw holes 101, 102, 103) are provided at one end. Distal apertures or holes 105, 106, 107 (distal fixation holes or distal screw holes 105, 106, 107) are provided at the opposite end. An intermediate apertures or hole 104 (intermediate fixation hole or intermediate screw hole 104) is provided between the proximal and distal holes, but nearer to the proximal end of the bone plate 100 (i.e., nearer to the proximal screw holes 101, 102, 103).

In an exemplary high tibial open wedge osteotomy, the bone plate 100 is secured to the proximal portion of the tibia (i.e., the portion "above" the medial opening) with fixation devices (screws) inserted through the proximal holes 101, 102, 103 and the intermediate hole 104. Similarly, the bone plate 100 is secured to the distal portion of the tibia (i.e., the portion "below" the medial opening) with fixation devices (screws) inserted through distal holes 105, 106, 107.

Figure 2:
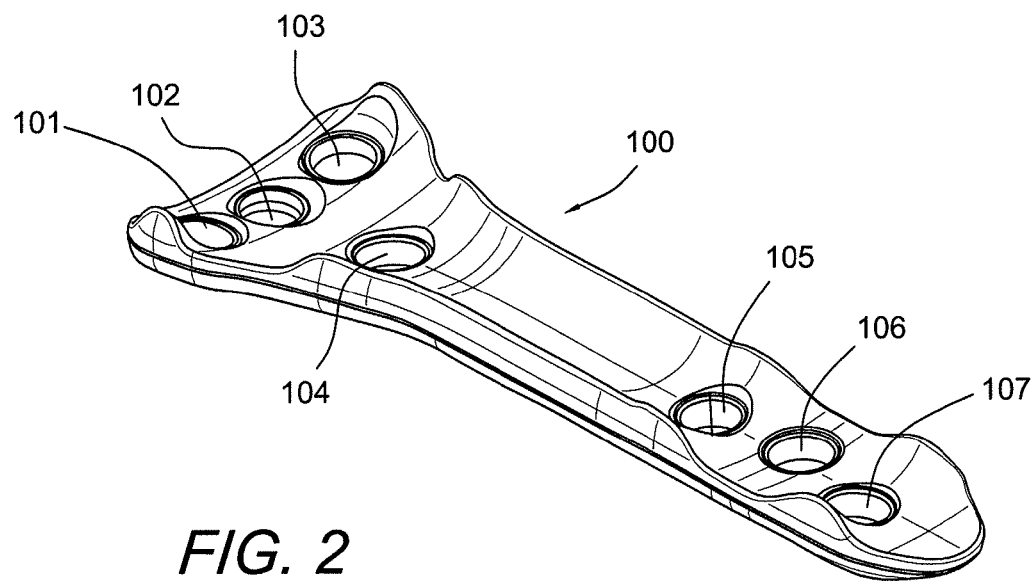
FIG. 2 is a perspective view of the underside of the bone plate illustrated in FIG. 1.
Figure 3:
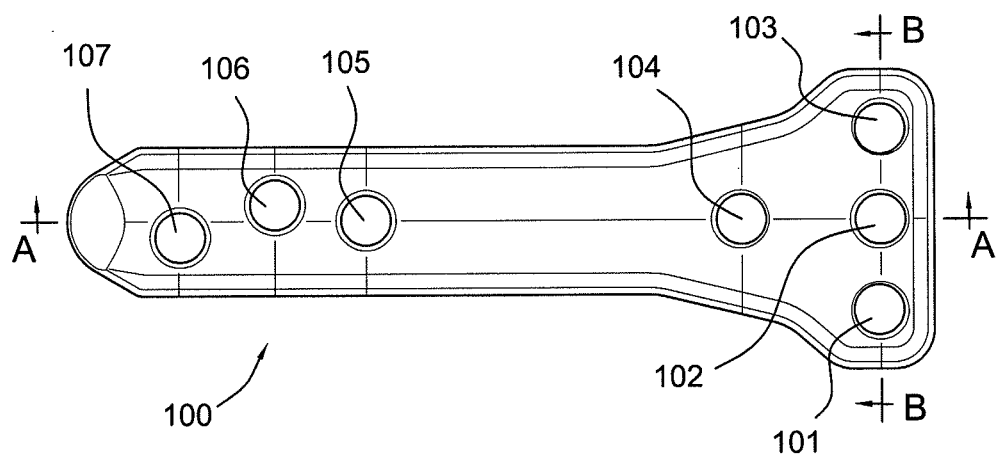
FIG. 3 is a plan view of the bone plate illustrated in FIG. 1.
Figure 4:
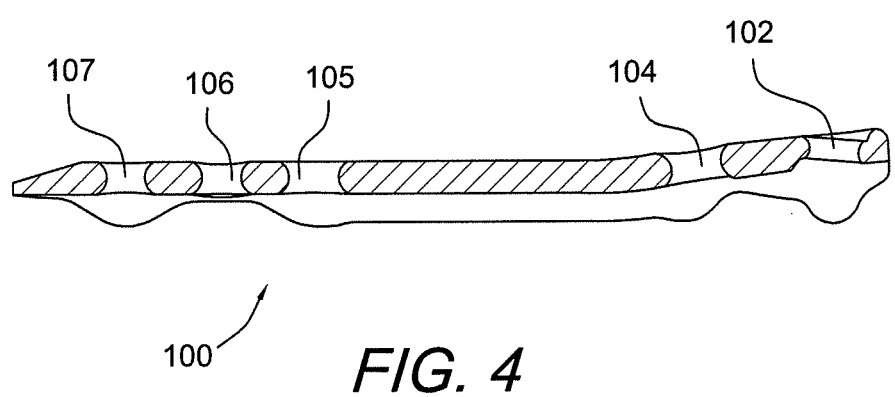
FIG. 4 is cross section of the bone plate along line A-A of FIG. 3.
Figure 5:
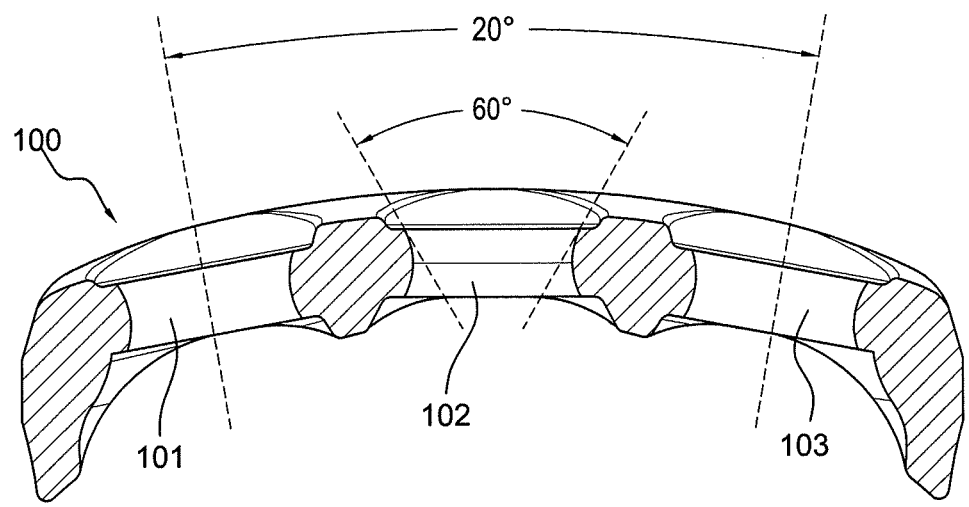
FIG. 5 is cross section of the bone plate along line B-B of FIG. 3.

FIG. 2 illustrates the underside of the bone plate 100 (i.e., the side facing the bone after installation). FIG. 3 is a plan view of the top of the bone plate 100. FIG. 4 is a cross section of the bone plate 100 along line A-A of FIG. 3. FIG. 5 is a cross section of the bone plate 100 along line B-B of FIG. 3. In a preferred embodiment, lines drawn through the center axis of proximal screw holes 101 and 102 form a 20° angle, as shown in FIG. 5. Also in a preferred embodiment, lines drawn tangent to opposite sides of the uppermost portion of the interior curved surface of the screw holes form a 60° angle. FIG. 5 illustrates this angle with respect to proximal screw hole 102, though the same angle can be formed in any or all of the other distal, intermediate, or proximal screw holes. The diameter of the screw holes in the bone plate is preferably less than the diameter of the fixation devices (screws) intended to be inserted through them. In this manner, the fixation screws can deform the interior walls of the screw holes, thereby "self-threading" the holes at an advantageous angle, as described above.

Figure 6:
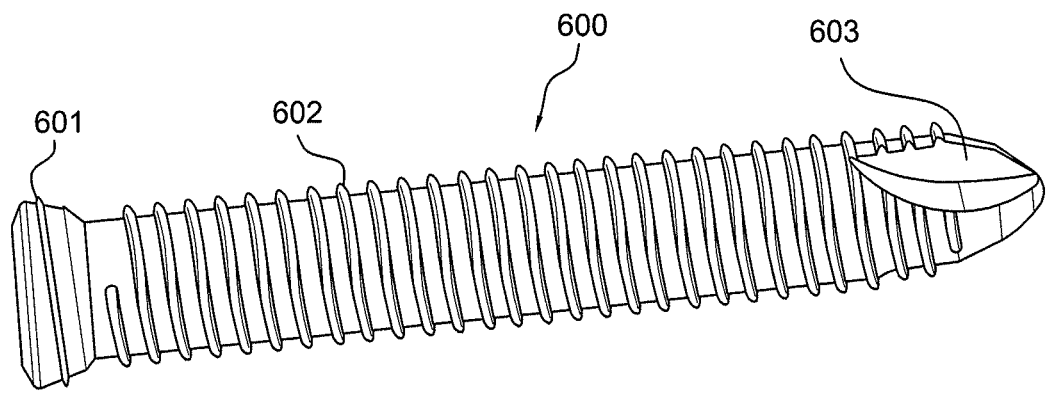
FIG. 6 is a perspective view of a screw used to fix the bone plate of FIG. 1 to a bone, in accordance with a disclosed embodiment.
Figure 7:
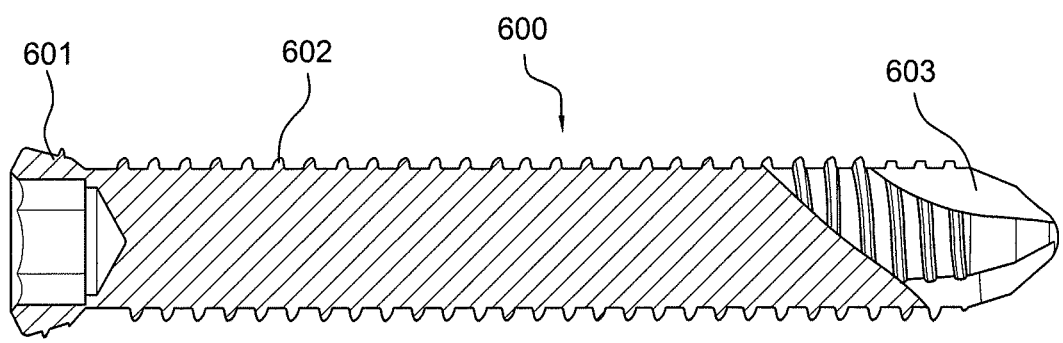
FIG. 7 is longitudinal cross section of the screw illustrated in FIG. 6.
Figure 8:
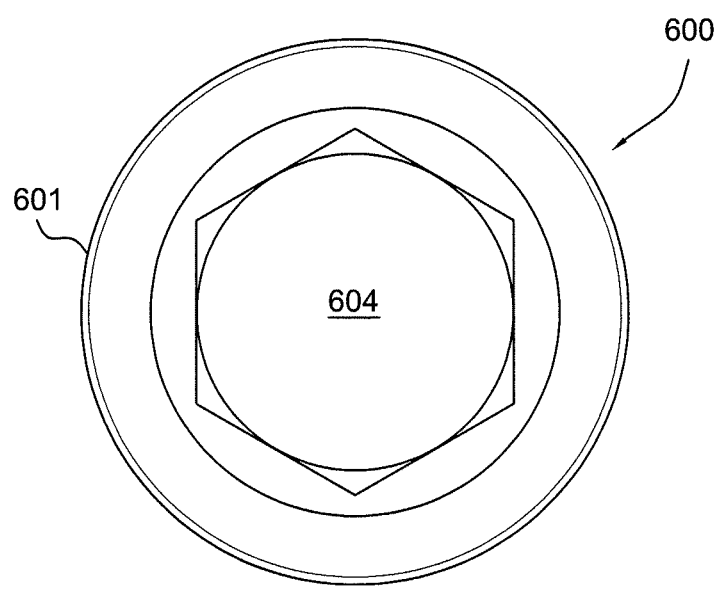
FIG. 8 is a plan view of the socket end of the screw illustrated in FIG. 6.
Figure 9:
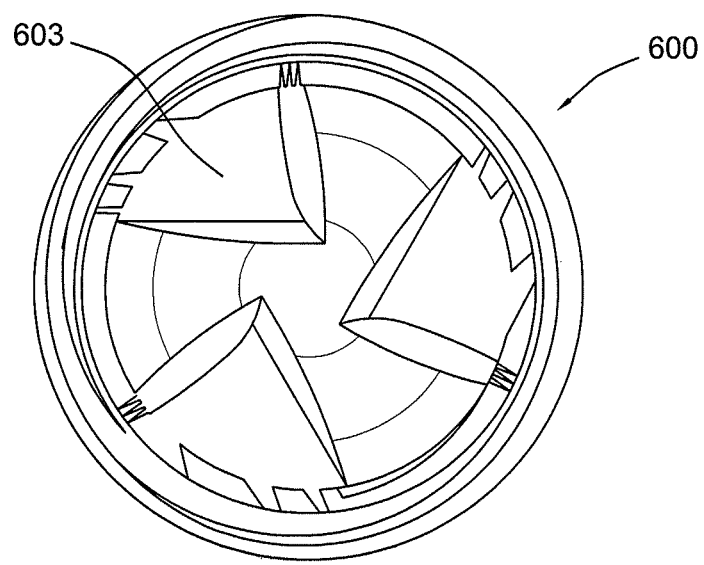
FIG. 9 is a plan view of the cutting end of the screw illustrated in FIG. 6.

FIG. 6 illustrates a fixation device 600 (screw 600) that can be used to fasten a bone plate of the present invention (such as bone plate 100, 200) to a bone. The fixation device 600 comprises a socket end 601 and a cutting end 603. The body of the fixation device 600 contains threads 602. FIG. 7 is a partial cross section along the longitudinal axis of the fixation device 600. FIG. 8 illustrates the socket end 601 of the fixation device 600. The socket end 601 comprises an interior portion 604 shaped to accommodate a tool for rotating the fixation device 600. In a preferred embodiment, the interior portion 604 defines a substantially hexagonal region. FIG. 9 illustrates the cutting end 603 of the fixation device 600. The threaded portion of the fixation device 600 is preferably 5.0 mm in diameter with 1.0 mm pitch between threads. In an exemplary embodiment, the fixation devices (such as screw 600) comprise titanium, most preferably in the form of $TiAl_6V_4$ (i.e., a titanium alloy comprising about 6% aluminum and 4% vanadium).

Figure 10:
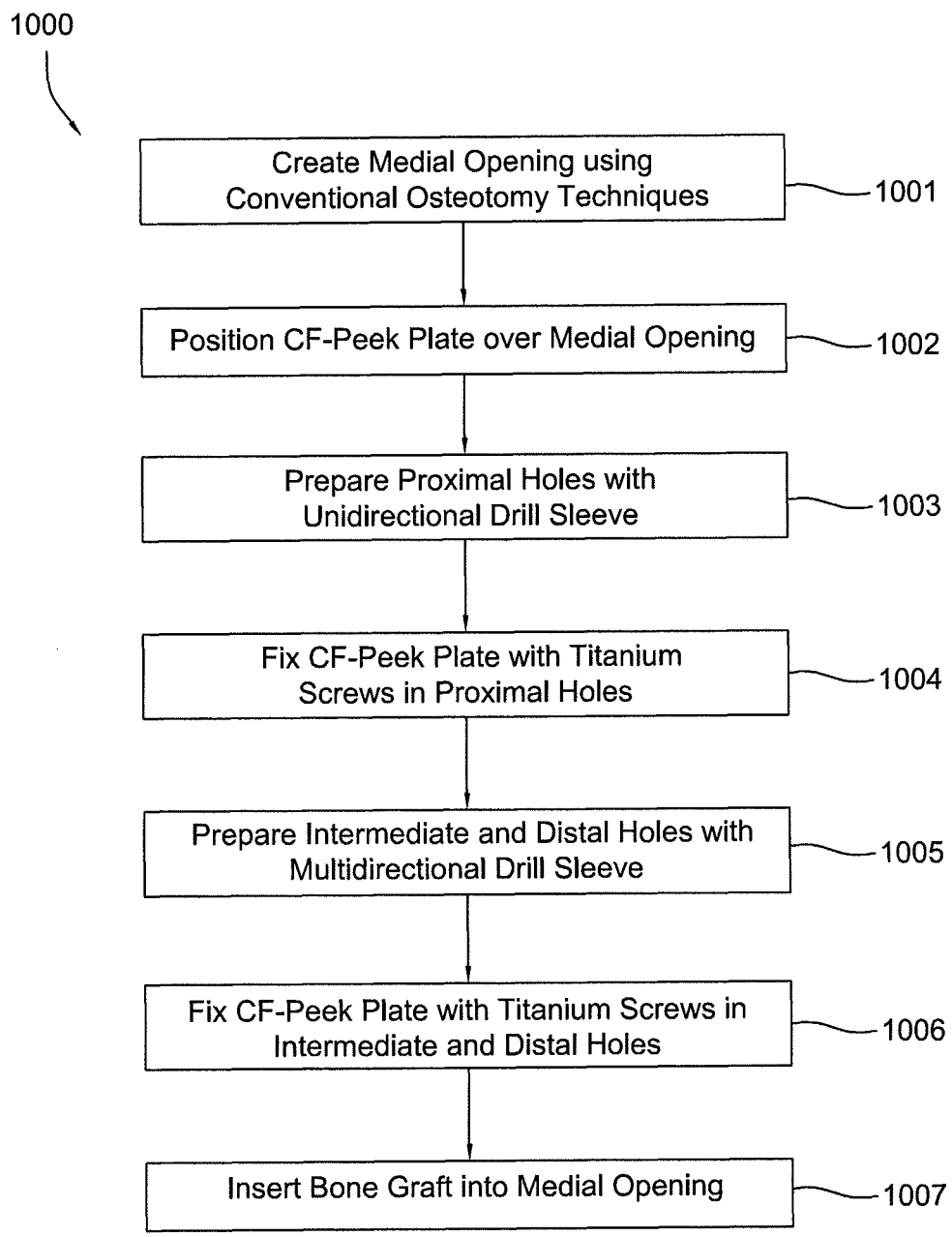
FIG. 10 is a flow chart of a method for performing high tibial open wedge osteotomy in accordance with a disclosed embodiment.
Figure 11:
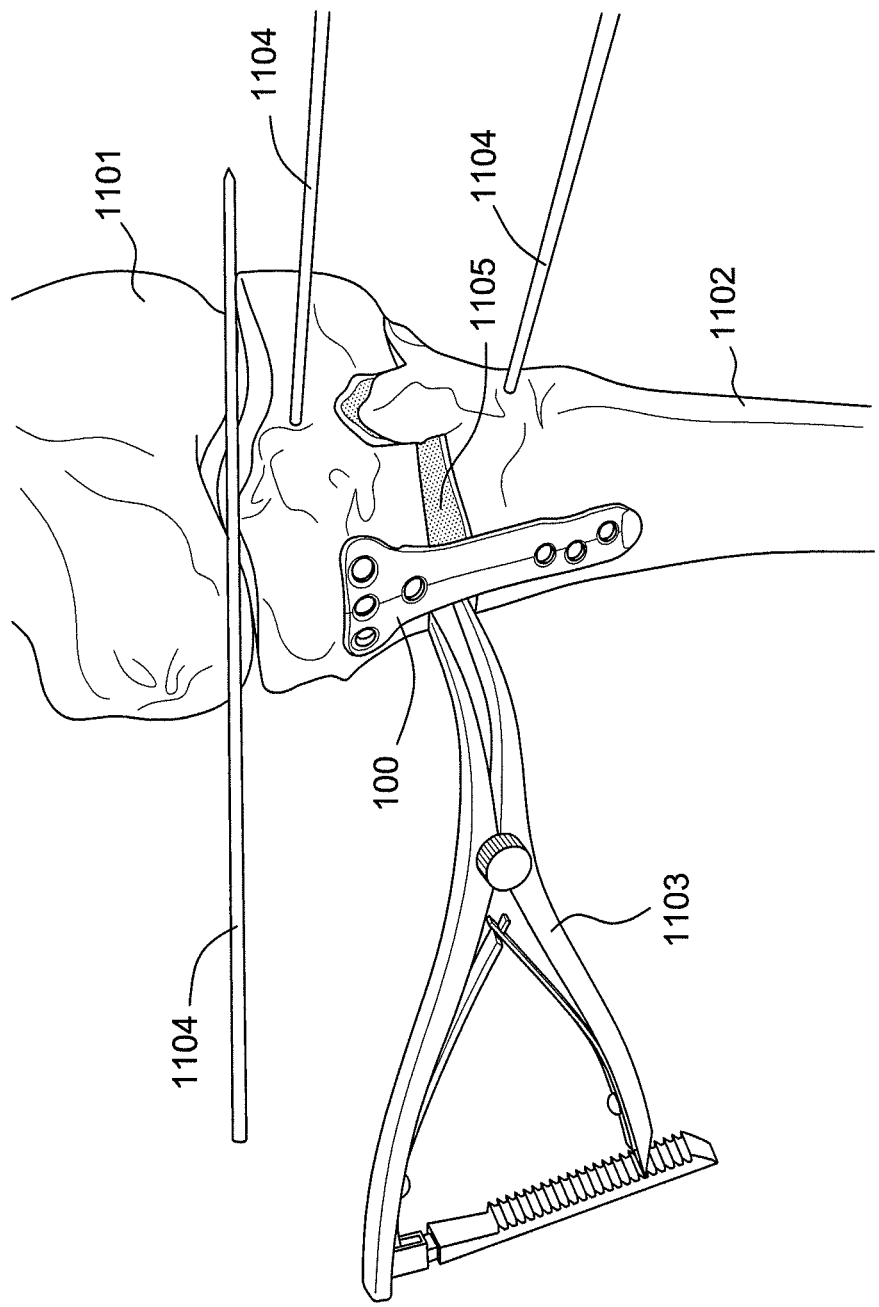
FIG. 11 illustrates the bone plate of FIG. 1 positioned over the medial opening during a high tibial open wedge osteotomy.

FIG. 10 is a flow chart illustrating steps of a method for performing high tibial open wedge osteotomy using the bone plate and fixation devices disclosed in this application. At step 1001, a medial opening is formed using conventional surgical techniques, such as described in U.S. Pat. No. 5,620,448 referenced above, for example. At step 1002, the bone plate 100 is positioned over the medial opening. FIG. 11 illustrates a femur 1101 and tibia 1102 at this stage of the osteotomy (i.e., after step 1002). Pliers 1103 may be used to hold the medial opening 1105 at an appropriate angle while the bone plate 100 is positioned over the medial opening 1105. Kirschner wires (also known as "K wires") 1104 may be used to provide orientation around the joint during the procedure.

Figure 12:
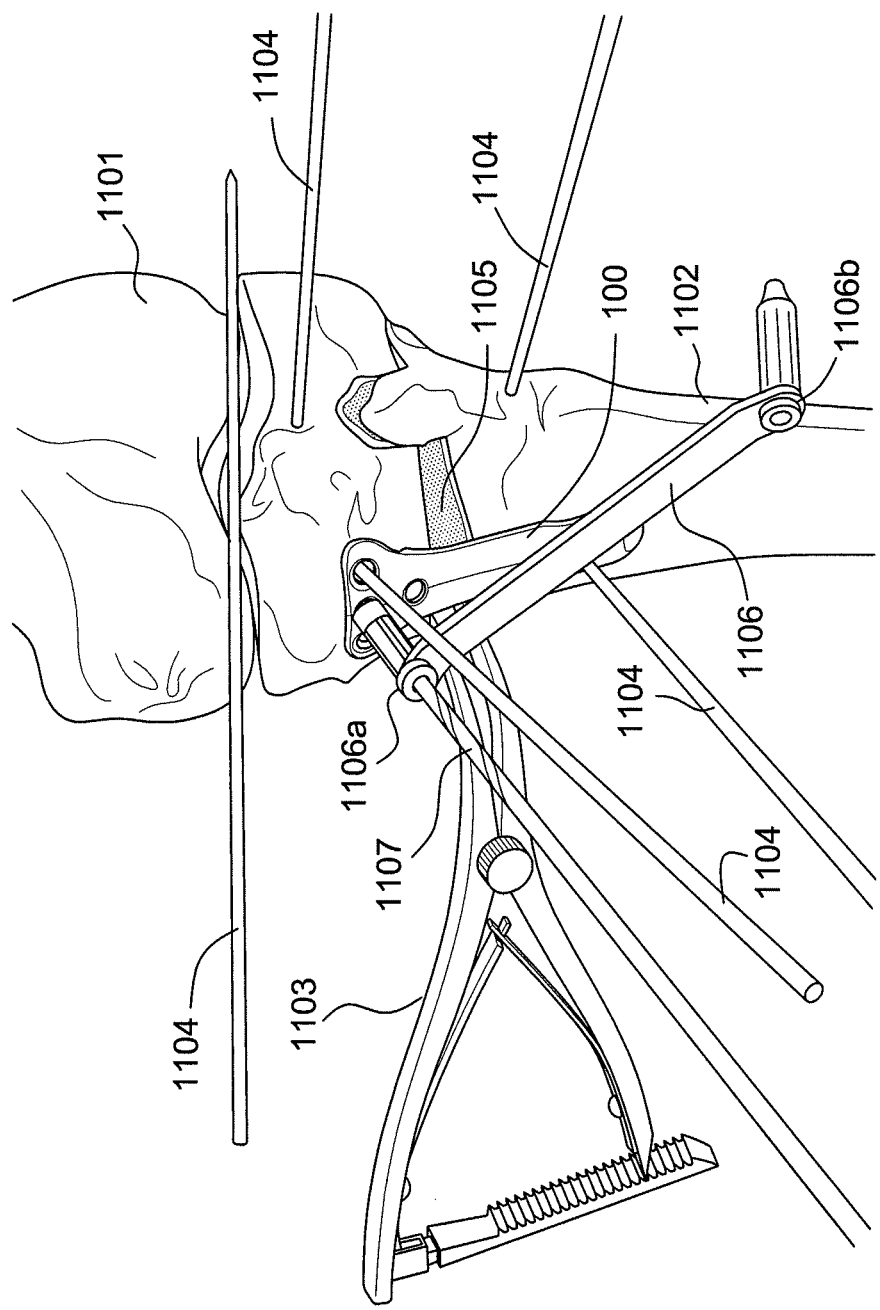
FIG. 12 illustrates temporary fixation of the bone plate of FIG. 1 over the medial opening and preparation of a proximal hole of the bone plate of FIG. 1 with a unidirectional drill sleeve.

At step 1003, guide holes are drilled into the tibia 1102 through the proximal screw holes 101, 102, 103 of the bone plate 100 using the unidirectional end 1106a of a drill sleeve 1106, as illustrated in FIG. 12. The unidirectional end 1106a acts as a guide for the drill bit 1107 and maintains the drill bit 1107 at a fixed angle with respect to the bone plate 100. K wires 1104 can be inserted into the tibia through any of the screw holes in bone plate 100 to temporarily fix the bone plate 100 in position, as also illustrated in FIG. 12. At step 1004, fixation screws, such as those described above with reference to FIGS. 6-9, are inserted through the proximal holes 101, 102, 103 and into the guide holes drilled at step 1003 to permanently fix the bone plate 100 to the proximal portion of the tibia 1102.

Figure 13:
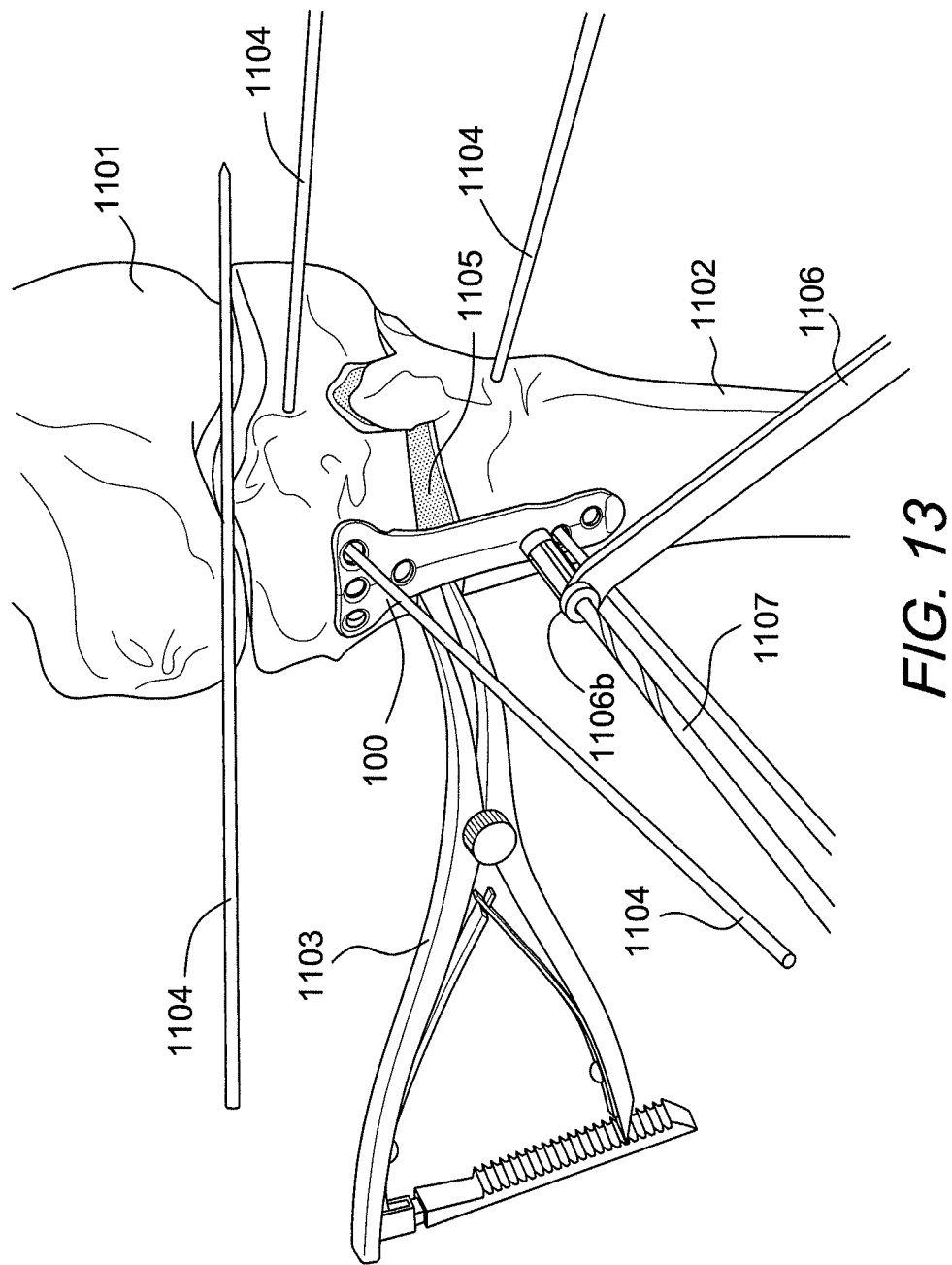
FIG. 13 illustrates preparation of a distal hole of the bone plate of FIG. 1 with a multidirectional drill sleeve.

At step 1005, guide holes are drilled into the tibia 1102 through the intermediate screw hole 104 and distal screw holes 105, 106, 107 of the bone plate 100 using the multidirectional end 1106b of the drill sleeve 1106, as illustrated in FIG. 13. Like the unidirectional end 1106a, the multidirectional end 1106b also acts as a guide for the drill bit 1107. However, the multidirectional end 1106b allows the drill bit 1107 to pivot within the intermediate screw hole 104 and distal screw holes 105, 106, 107. At step 1006, fixation screws are inserted through the intermediate screw hole 104 and distal screw holes 105, 106, 107 and into the guide holes drilled at step 1005 to permanently fix the bone plate 100 to the distal portion of the tibia 1102.

The sequence of drilling and screw insertion steps described herein is merely exemplary. The order can be varied based on the professional judgment of the surgeon performing the osteotomy. For example, a guide hole could be drilled through one of the distal screw holes 105, 106, 107 before guide holes are drilled through all of the proximal screw holes 101, 102, 103. Similarly, a screw might be inserted through one or more of the distal screw holes 105, 106, 107 before additional screws are inserted through all of the proximal holes 101, 102, 103. In addition, the multidirectional end 1106b of the drill sleeve 1106 may be used in conjunction with the proximal screw holes 101, 102, 103 of the bone plate 100, and the unidirectional end 1106a of the drill sleeve 1106 may be used in conjunction with the intermediate hole 104 and distal holes 105, 106, 107 of the bone plate 100, as necessary to achieve advantageous alignment of the fixation devices (screws).

Figure 14:
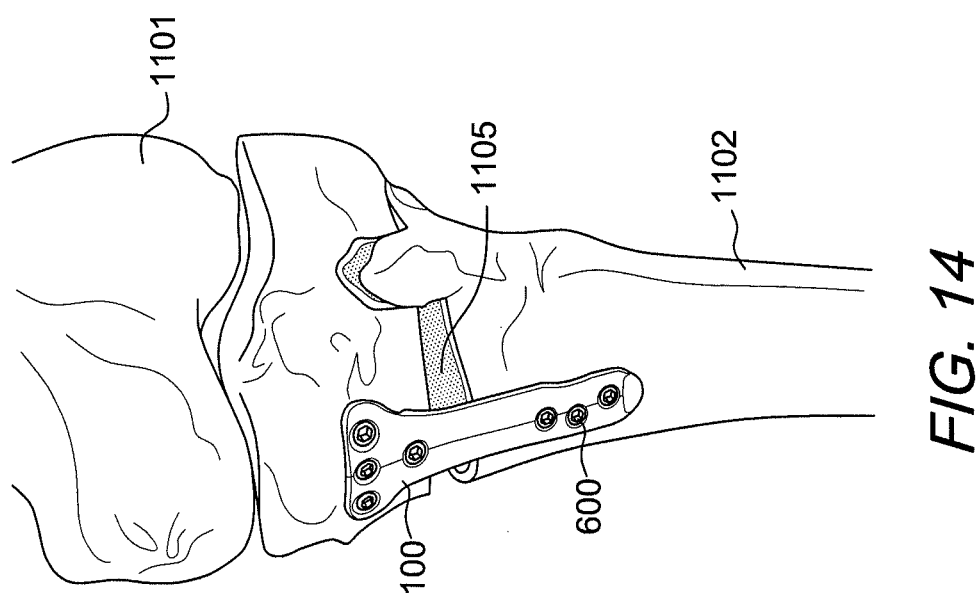
FIG. 14 illustrates the bone plate of FIG. 1 fixed over the medial opening with a plurality of the screws illustrated in FIG. 7.
Figure 15:
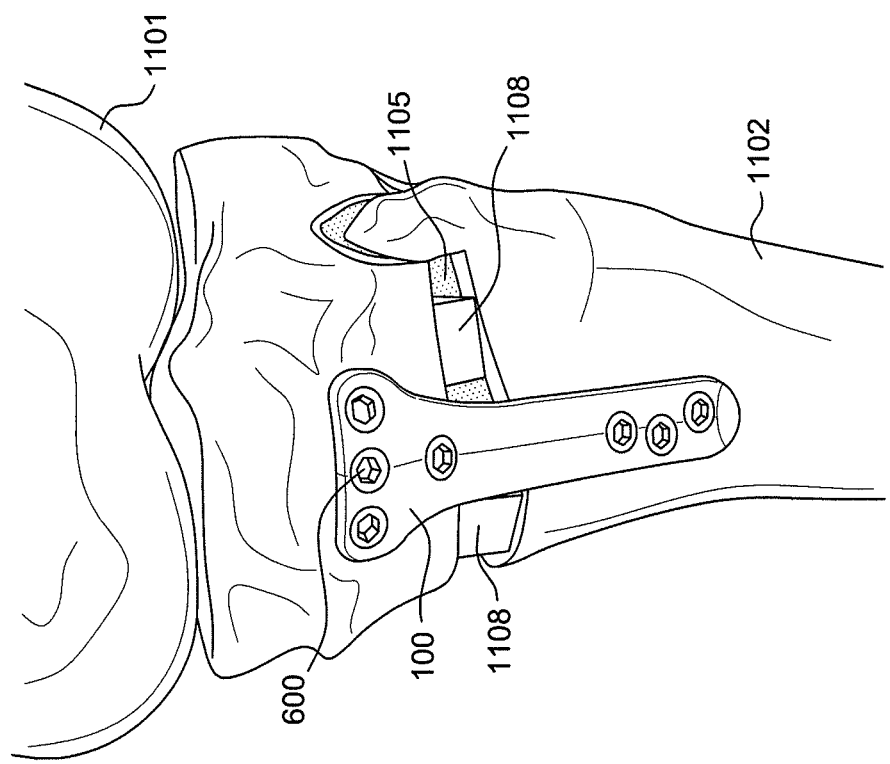
FIG. 15 illustrates the insertion of bone grafts into the medial opening.
Figure 16:
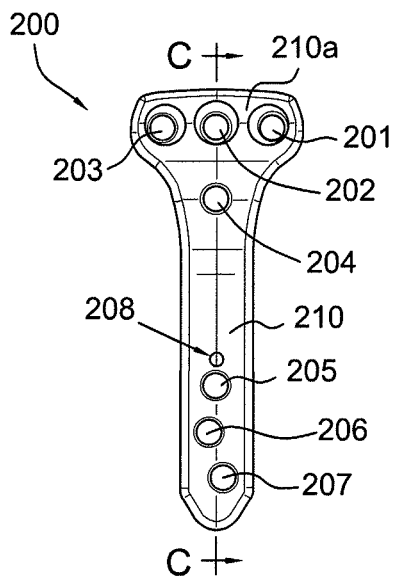
FIG. 16 is a top plan view of a bone plate according to a second embodiment of the present invention.
Figure 17:
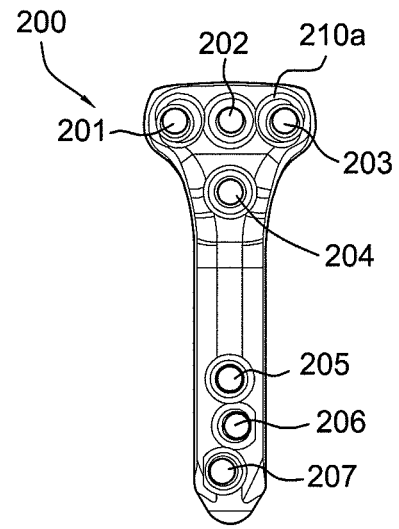
FIG. 17 is a top view of the underside of the bone plate of FIG. 16.

FIG. 14 illustrates the tibia 1102 and the bone plate 100 after completion of step 1006. As shown, fixation screws 600 have been inserted into the guide holes drilled at steps 1003 and 1005 to permanently fix the bone plate 100 to the tibia 1102. At step 1007, bone grafts may be inserted into the medial opening to promote bone growth. U.S. Pat. No. 6,823,871, which is assigned to Arthrex, Inc. and incorporated herein by reference, discloses example grafts and graft materials suitable for insertion into osteotomy openings. In general, local tibial cancellous grafts may be used for defects measuring 7.5 mm of less. Bi- or tri-cortical iliac crest autografts or allografts or synthetic bone void filler could be used for defects larger than 7.5 mm. FIG. 15 illustrates the tibia 1102 after completion of step 1007. As shown, bone grafts 1108 have been inserted into the medial opening 1105.

Figure 18:
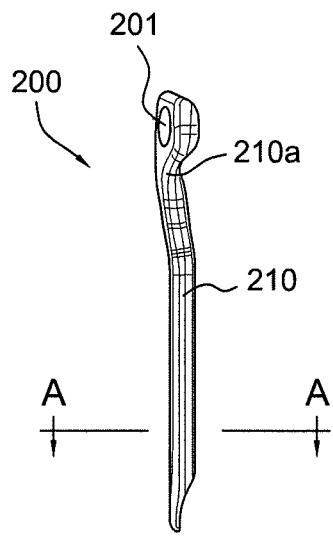
FIG. 18 is a side view of the bone plate of FIG. 16.
Figure 19:
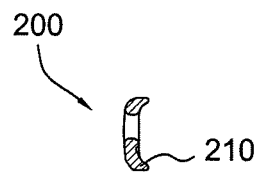
FIG. 19 is a cross-sectional view of the bone plate of FIG. 18 taken along line A-A.
Figure 20:
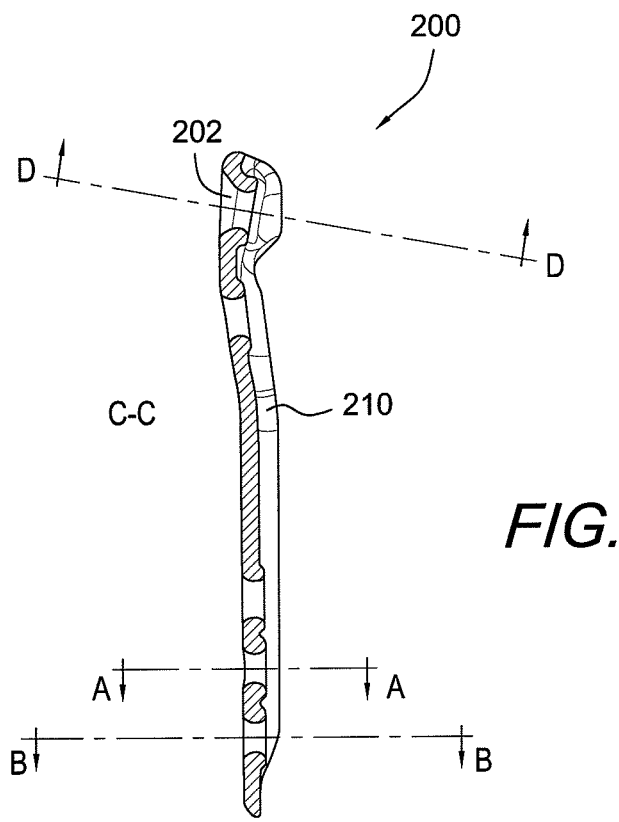
FIG. 20 is a cross-sectional view of the bone plate of FIG. 16 taken along line C-C.
Figure 21:
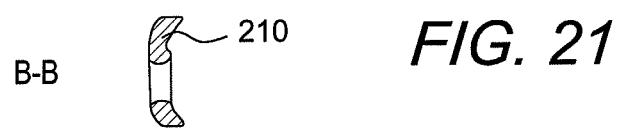
FIG. 21 is a cross-sectional view of the bone plate of FIG. 20 taken along line B-B.
Figure 22:
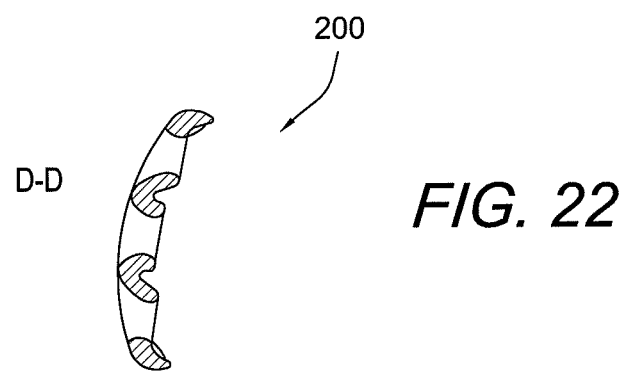
FIG. 22 is a cross-sectional view of the bone plate of FIG. 20 taken along line D-D.

FIGS. 16-22 illustrate a bone plate 200 according to another embodiment of the present invention. Bone plate 200 may be also employed in conjunction with fixation devices such as fixation device (screw) 600 described above. Bone plate 200 is similar in part to bone plate 100 in that bone plate 200 also comprises carbon fiber reinforced PEEK and is also provided with fixation apertures or holes with rounded, curved interior walls (i.e., non-threaded holes) that allow corresponding fixation devices (such as fixation screws 600, for example) to be inserted at various angles. Bone plate 200 has a more convex configuration, however, as illustrated in FIG. 18, for example, where proximal portion 210a of body plate 210 is curved inwardly to allow through hole or aperture 201 to be visible when the plate 200 is viewed from the lateral side. In this manner, bone plate 200 is designed to better accommodate the curvature of a patient's bone, while allowing the fixation devices to be inserted at different angles as described above with reference to bone plate 100.

While embodiments have been described in detail in connection with the examples known at the time, it should be readily understood that they are not limited to such disclosed embodiments. Rather, they can be modified to incorporate any number of variations, alterations, substitutions, or equivalent arrangements not heretofore described. Accordingly, it is not intended that the present invention be limited to the illustrated embodiments, but only by the appended claims.

What is claimed as new and desired to be protected by Letters Patent of the United States is:

1. A method of open wedge osteotomy, comprising the steps of:
    forming an opening in tibia;
    providing a bone plate to accommodate fixation devices inserted at various angles, the bone plate having a body with a first surface, a second surface opposed to the first surface, the body comprising carbon fiber reinforced polyetheretherketone, the body having a proximal region and a distal region, the proximal region comprising a first plurality of apertures passing through the plate, and the distal region comprising a second plurality of apertures passing through the plate, wherein each of the first and second plurality of apertures is a through hole with a longitudinal axis and comprising non-threaded, rounded and curved internal walls that accommodate a threaded metallic fixation device, the first and second plurality of apertures accommodating threaded metallic fixation devices inserted at a range of angles relative to the first and second plurality of apertures and non-parallel to the longitudinal axis of each through hole, wherein the non-threaded, rounded internal walls have a uniform configuration along the longitudinal axis of each through hole, and wherein each of the threaded fixation devices has a first uniform diameter, and wherein each of the first and second plurality of apertures has a second uniform diameter, the second diameter being smaller than the first diameter, to allow the threaded metallic fixation device to deform the smooth, non-threaded internal walls of the first and second plurality of apertures upon insertion, for securing the bone plate to the bone, and wherein the body of the plate is formed of a material softer than a material of the threaded metallic fixation device;

positioning the bone plate over the opening in the tibia;

forming proximal holes in the tibia with unidirectional drill sleeve and through the first plurality of apertures of the proximal region of the bone plate;

forming intermediate and distal holes in the tibia with multidirectional drill sleeve and through the second plurality of apertures of the distal region of the bone plate; and inserting the threaded fixation devices through the first and second plurality of apertures, so that threads of the threaded fixation devices deform and thread the non-threaded internal walls of the first and second plurality of apertures upon insertion and self-thread the through holes at an angle, to secure the bone plate to the tibia.

2. The method of claim 1, wherein the body consists essentially of carbon fiber reinforced polyetheretherketone.

3. The method of claim 1, wherein the fixation device is formed of at least one metal.

4. The method of claim 1, wherein the fixation device comprises $TiAl_6V_4$.

5. The method of claim 1, wherein the fixation device comprises $TiAl_6V_4$ with about 6% aluminum and about 4% vanadium.

6. The method of claim 1, wherein the internal walls are about parallel to a longitudinal axis of the body.

7. The method of claim 1, wherein the body has a T-shape configuration.

8. The method of claim 1, wherein the proximal region of the body has a convex configuration.

9. The method of claim 1, wherein the second plurality of apertures extend non-symmetrically relative to a longitudinal axis of the body.

10. The method of claim 1, wherein the first plurality of apertures are through holes with rounded edges.

11. The method of claim 1, wherein the second plurality of apertures are through holes with rounded edges.

12. The method of claim 1, wherein the fixation device is selected from the group consisting of a washer, a screw and an anchor.

13. The method of claim 1, wherein the fixation device is a $TiAl_6V_4$ screw.

14. The method of claim 1, wherein the fixation device comprises a material selected from the group consisting of titanium, titanium alloy and stainless steel.

15. The method of claim 1, further comprising the step of inserting an additional fixation device at an angle different from the insertion angle of the threaded fixation device.

* * * * *